United States Patent
Quan et al.

(10) Patent No.: US 7,247,289 B2
(45) Date of Patent: Jul. 24, 2007

(54) POROUS ALUMINUM FLUORIDE

(75) Inventors: Hengdao Quan, Ibaraki (JP); Masanori Tamura, Ibaraki (JP); Akira Sekiya, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 87 days.

(21) Appl. No.: 10/535,491

(22) PCT Filed: Nov. 12, 2003

(86) PCT No.: PCT/JP03/14357

§ 371 (c)(1),
(2), (4) Date: May 18, 2005

(87) PCT Pub. No.: WO2004/045763

PCT Pub. Date: Jun. 3, 2004

(65) Prior Publication Data

US 2006/0025639 A1    Feb. 2, 2006

(30) Foreign Application Priority Data

Nov. 19, 2002    (JP) ............................... 2002-334883

(51) Int. Cl.
*C01B 21/72*    (2006.01)
*C07C 69/63*    (2006.01)
*C07C 5/00*    (2006.01)

(52) U.S. Cl. ........................ 423/412; 560/227; 585/935
(58) Field of Classification Search ..................... None
See application file for complete search history.

(56) References Cited

U.S. PATENT DOCUMENTS 3,907,913 A * 9/1975 Kemp ......................... 585/371

FOREIGN PATENT DOCUMENTS

EP         999 195          5/2000

OTHER PUBLICATIONS

Lalancette et al. (1973) Intercalation of Antimony Pentafluoride in the Lattice of Graphite, J.C.S. Chem. Comm. p. 815.
McKee et al. (1999) Properties of Graphite-Antimony Pentafluoride and Graphite-Arsenic Pentafluoride Intercalation Compounds, Ext. Abstr. Program - Bienn. Conf.Carbon, 14, 276-7 (abstract).

* cited by examiner

*Primary Examiner*—Paul A. Zucker
(74) *Attorney, Agent, or Firm*—Morgan, Lewis & Bockius LLP

(57) ABSTRACT

A porous aluminum fluoride on which $SbCl_xF_{5-x}$ (wherein x represents a numeral of 0 to 5) is supported, $SbCl_xF_{5-x}$ being obtainable by supporting $SbCl_5$, or the like on a porous aluminum fluoride and treating it with hydrogen fluoride. The resulting porous aluminum fluoride has a high activity as a fluorinating agent, a fluorination catalyst, or the like, is easy to handle, can be used for a flow-type reaction, and also can be used even at a high temperature.

8 Claims, 2 Drawing Sheets

POROUS ALUMINUM FLUORIDE

TECHNICAL FIELD

The present invention relates to a porous aluminum fluoride and a fluorination catalyst, a fluorinating agent, a dehalogenating agent comprising the same.

BACKGROUND ART

Fluorine-containing compounds are widely utilized for industrial use such as polymer materials, coolants, cleaning agents, foaming agents, medicaments and pesticides. In particular, hydrofluorocarbons are used as refrigerants, foaming agents, and cleaning agents as alternative substances to chlorofluorocarbons. Moreover, fluorine-containing esters are expected to have uses as alternatives to electrolytes for lithium batteries.

Such fluorine-containing compounds are usually synthesized by utilizing fluorinating agents or fluorination catalysts such as antimony fluoride with organohalogen compounds such as hydrochlorocarbons.

However, since antimony pentafluoride is hygroscopic, there is a disadvantage that it emits smoke in a highly humid air and thus is difficult to handle (cf. Non-Patent Document 1).

In order to solve such a problem, there is proposed a method for making its handling easy by heating antimony pentafluoride and supporting it on graphite (cf. Non-Patent Document 2). However, since graphite is powdery, the product is not necessarily suitable for a flow-type reaction and also its activity tends to decrease under a reaction condition of high temperature owing to sublimation of antimony pentafluoride.

Non-Patent Document 1:

McKee, D. W.; Interrante, L. V.; Markiewicz, R. S., *Program-Bienn. Conf. Carbon*, 14, 276-7 (1979))

Non-Patent Document 2:

Lalancette, J. M.; Lafontaine, J., *J. C. S. Chem. Comm.*, 815 (1973))

DISCLOSURE OF THE INVENTION

An object of the present invention is to provide a novel porous aluminum fluoride which has a high activity as a fluorinating agent, a fluorination catalyst, or the like, is easy to handle, can be used for a flow-type reaction, and also can be used even at a high temperature.

As a result of extensive studies for solving the above problems, the present inventors have found that a fluorinating agent or a catalyst which has a high activity, is easy to handle, and can be used even at a high temperature is obtainable by supporting antimony pentafluoride on a porous aluminum fluoride and fluoro compounds and esters such as hydrofluorocarbons can be produced using the same. Accordingly, they have accomplished the present invention Namely, according to the present invention, the following inventions are provided.

(1) A porous aluminum fluoride on which $SbCl_xF_{5-x}$ (wherein x represents a numeral of 0 to 5) is supported.
(2) A process for producing the porous aluminum fluoride according to the above (1), which comprises supporting $SbCl_yF_{5-y}$ (wherein y represents a numeral of 0 to 5) on a porous aluminum fluoride and treating it with hydrogen fluoride.
(3) A fluorination catalyst comprising the porous aluminum fluoride according to the above (1).
(4) A fluorinating agent comprising the porous aluminum fluoride according to the above (1).
(5) A dehalogenating agent comprising the porous aluminum fluoride according to the above (1).
(6) A process for producing a fluoro compound represented by the formula (2): $R^1R^2R^3CF$ (wherein $R^1$, $R^2$ and $R^3$ each represents hydrogen, a halogen, an alkyl group which may be substituted with a halogen or an ether group, or an alkoxy group; or $R^1$, $R^2$, and $R^3$ may be combined with each other to form a ring), which comprises reacting a compound represented by the formula (1): $R^1R^2R^3CX$ (wherein $R^1$, $R^2$, and $R^3$ have the same meanings as described above; and X represents chlorine, bromine, or iodine) with hydrogen fluoride in the presence of the catalyst according to the above (3).
(7) A process for producing a fluoro compound represented by the formula (2): $R^1R^2R^3CF$ (wherein $R^1$, $R^2$ and $R^3$ have the same meanings as described above), which comprises reacting a compound represented by the formula (1): $R^1R^2R^3CX$ (wherein $R^1$, $R^2$, $R^3$ and X have the same meanings as described above) with the fluorinating agent according to the above (4).
(8) A process for producing an ester represented by the formula (4): $R^1CH_2O(CO)R^2$ (wherein $R^1$ represents hydrogen or an alkyl group which may be substituted with a halogen; and $R^2$ represents hydrogen or an alkyl group which may be substituted with a halogen), which comprises reacting an ether compound represented by the formula (3): $R^1CH_2OCXYR^2$ (wherein $R^1$ and $R^2$ have the same meanings as described above; X represents fluorine or chlorine; and Y represents fluorine or chlorine) with the dehalogenating agent according to the above (5).

BEST MODE FOR CARRYING OUT THE INVENTION

Figure 1:
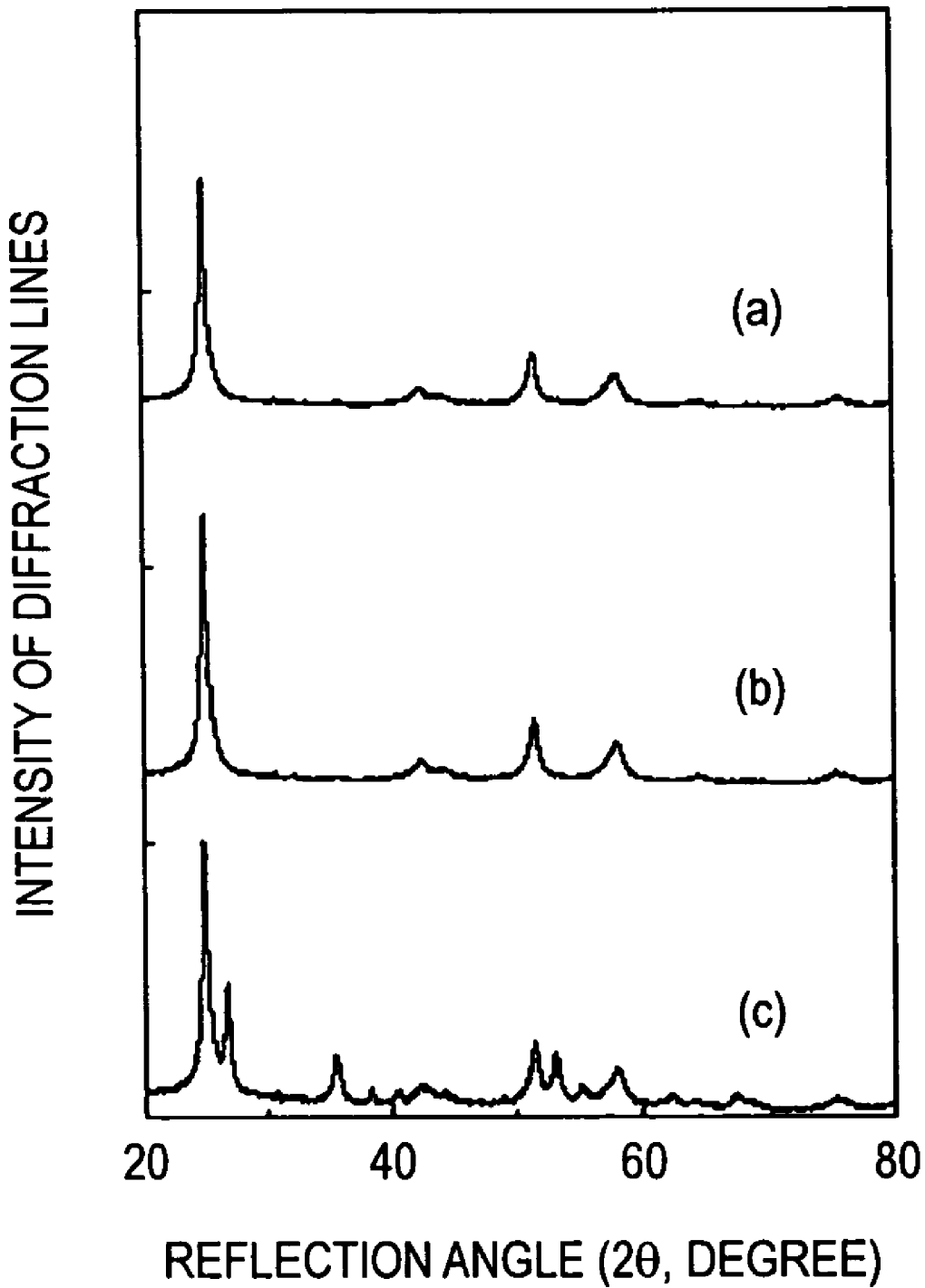
FIG. 1 is an X-ray diffraction pattern of PAF, Sb—F/PAF (A), and Sb—F/PAF(B).

The porous aluminum fluoride of the present invention on which $SbCl_xF_{5-x}$ (wherein x represents a numeral of 0 to 5) is supported (hereinafter also referred to as antimony fluoride-supported aluminum fluoride) is produced, for example, by supporting antimony pentachloride on a porous aluminum fluoride and subsequently treating it with hydrogen fluoride.

Although all of hitherto known aluminum fluorides can be used as the aluminum fluoride to be used as a starting material, it is not necessarily a pure fluoride and may be a fluoride partially containing oxygen or may be a mixture with other metal salt(s).

The porous aluminum fluoride preferably used in the present invention has a particle size of 0.1 mm to 10 mm, and preferably 0.2 mm to 5 mm; a surface area of 1 m²/g to 400 m²/g, and preferably 30 m²/g to 200 m²/g; a pore size of 5 Å to 300 Å, and preferably 10 Å to 200 Å; and a pore volume of 0.05 cm³/g to 1.0 cm³/g, and preferably 0.1 cm³/g to 0.8 cm³/g.

As the method for supporting $SbCl_yF_{5-y}$ (wherein y represents a numeral of 0 to 5) on a porous aluminum fluoride, there may be mentioned a method of adding it dropwise to the aluminum fluoride, a method of adding a solution of antimony pentachloride dropwise to the aluminum fluoride or mixing the solution with the aluminum fluoride and then removing the solvent under reduced pressure or by heating, and the like, and the former method is preferable because of the easiness of operations. In this connection, it is preferable to use antimony pentachloride as $SbCl_yF_{5-y}$ (wherein y represents a numeral of 0 to 5).

At the treatment with hydrogen fluoride, it is sufficient to bring hydrogen fluoride into contact with the above porous aluminum fluoride on which antimony halide has been supported, and the method is not particularly limited. For example, there may be mentioned a method of bringing hydrogen fluoride gas into contact with the porous aluminum fluoride on which antimony pentachloride has been supported at a predetermined temperature, a method of adding a predetermined amount of hydrofluoric acid to the porous aluminum fluoride on which antimony pentachloride has been supported and removing the solvent by evaporation, and the like. Among these, in view of possible efficient production of anhydrous antimony fluoride-supported salts, the former method is preferable. In this case, hydrogen fluoride diluted with nitrogen gas or argon gas can be also used.

The treatment with hydrogen fluoride is carried out at a temperature of 10° C. to 300° C., and preferably 100° C. to 200° C. The amount of hydrogen fluoride is not particularly limited. By the treatment with hydrogen fluoride, antimony pentachloride is fluorinated but even when the chlorine is not entirely replaced with fluorine, the product can be used for fluorination reactions and the like. Namely, a product wherein $SbCl_xF_{5-x}$ (wherein x represents a numeral of 0 to 5) is supported on the porous aluminum fluoride exhibits a function as a fluorination catalyst, a fluorinating agent a dehalogenating agent, or the like.

The porous aluminum fluoride of the present invention on which $SbCl_xF_{5-x}$ (wherein x represents a numeral of 0 to 5) is supported has a structure that $SbCl_xF_{5-x}$ (wherein x represents a numeral of 0 to 5) is supported inside the pores of a porous aluminum fluoride as a starting material and the supported structure is, for example, confirmed by the measurement of the surface area and pore volume and instrumental analyses such as X-ray photoelectron spectroscopy and X-ray diffraction.

Moreover, the amount of $SbCl_xF_{5-x}$ (wherein x represents a numeral of 0 to 5) to be supported based on the starting porous aluminum fluoride is usually from 1 to 80% by weight, preferably from 10 to 60% by weight, and more preferably from 20 to 50% by weight.

The porous aluminum fluoride of the present invention on which $SbCl_xF_{5-x}$ (wherein x represents a numeral of 0 to 5) is supported is useful as a fluorination catalyst, a fluorinating agent, a dehalogenating agent, and the like. Representative application examples thereof are explained below.

Fluorination Catalyst:

The antimony fluoride-supported aluminum fluoride of the present invention can be suitably used as a catalyst for producing a fluoro compound represented by the formula (2): $R^1R^2R^3CF$ (wherein $R^1$, $R^2$, and $R^3$ each represents hydrogen, a halogen, an alkyl group which may be substituted with a halogen or an ether group, or, an alkoxy group; or $R^1$, $R^2$, and $R^3$ may be combined with each other to form a ring) by fluorinating a compound represented by the formula (1): $R^1R^2R^3CX$ (wherein $R^1$, $R^2$, and $R^3$ have the same meanings as described above; and X represents chlorine, bromine, or iodine) with hydrogen fluoride.

Examples of the compound represented by the above formula (1) include chloromethane, dichloromethane, trichloromethane, tetrachloromethane, chlorofluoromethane, dichlorofluoromethane, chlorodifluoromethane, chloroethane, 1,1-dichloroethane, 1,2-dichloroethane, 1,1,1-trichloroethane, 1,1,2-trichloroethane, 1,1,1,2-tetrachloroethane, 1,1,2,2-tetrachloroethane, 1-chloro-1,1,-difluoroethane, 1-chloro-1,2-difluoroethane, 1-chloro-2,2-difluoroethane, 1,1-dichloro-1-fluoroethane, 1,1-dichloro-2-fluoroethane, 1-chloro-2,2,2-trifluoroethane, and the like.

Moreover, when the compound represented by the above formula (1) is formed in the reaction system, the compound represented by the above formula (2) can be obtained. For example, since an unsaturated compound substituted with a halogen such as chlorine easily react with hydrogen fluoride in the reaction system to form the compound represented by the above formula (1), the compound represented by the above formula (2) can be obtained even when such an unsaturated compound is used as a starting substance.

Examples of the unsaturated compound include chloroethylene, 1,1-dichloroethylene, 1,2-dichloroethylene, trichloroethylene, tetrachloroethylene, 1,1-dichloro-2,2-difluoroethylene, trifluorochloroethylene, and the like.

Furthermore, in the case of a compound having plurality of halogens (except fluorine) in the molecule among the compounds represented by the above formula (1), one of the halogens is substituted with fluorine by the present reaction but the thus formed compound also belongs to the compound represented by the above formula (1), so that a polyfluoro compound can be obtained by the further fluorination reaction.

Hydrogen fluoride to be used in these catalytic fluorination reactions is advantageously used in an excess amount relative to the compound represented by the above formula (1). For example, it is suitable to use 1 mol or more, and preferably 3 mol to 10 mol, of hydrogen fluoride based on 1 mol of the compound represented by the above formula (1). In this case, hydrogen fluoride diluted with nitrogen gas or argon gas may be also used. The amount of the antimony fluoride-supported aluminum fluoride to be used as a catalyst is not particularly limited.

The reaction temperature of the fluorination reaction is from 100° C. to 400° C., and preferably 250° C. to 350° C. The mode of the reaction may be a batch type or a flow-type. In particular, in the antimony fluoride-supported aluminum fluoride of the present invention, a pellet-form aluminum fluoride support can be use and the activity does not decrease even at a high temperature of close to 400° C., so that the fluoride is particularly useful in a flow-type reaction.

Fluorinating Agent:

The antimony fluoride-supported aluminum fluoride of the present invention can be also suitably used as a fluorinating agent for producing a fluoro compound represented by the formula (2): $R^1R^2R^3CF$ (wherein $R^1$, $R^2_1$, and $R^3$ each represents hydrogen, a halogen, an alkyl group which may be substituted with a halogen or an ether group, or, an alkoxy group; or $R^1$, $R^2$, and $R^3$ may be combined with each other to form a ring) by fluorinating a compound represented by the formula (1): $R^1R^2R^3CX$ (wherein $R^1$, $R^2$, and $R^3$ have the same meanings as described above and X represents chlorine, bromine, or iodine).

The antimony fluoride-supported aluminum fluoride as the fluorinating agent may be suitably used in an excess amount relative to the compound represented by the above formula (1). For example, the fluoride may be used so that fluorine contained in the antimony fluoride-supported aluminum fluoride becomes 2 mol or more, and preferably from 2 mol to 50 mol, based on the compound represented by the formula (1).

The mode of the fluorination reaction is not particularly limited as far as the compound represented by the above formula (1) comes into contact with the antimony fluoride-supported aluminum fluoride. Moreover, a solvent may be used and an aliphatic hydrocarbon, an aromatic hydrocarbon, or the like can be used. The temperature of the fluorination reaction is from 10° C. to 400° C., and preferably from 50° C. to 350° C.

Dehalogenating Agent:

Furthermore, the antimony fluoride-supported aluminum fluoride of the present invention can also suitably be used as a dehalogenating agent for producing an ester represented by the formula (4): $R^1CH_2O(CO)R^2$ (wherein $R^1$ represents hydrogen or an alkyl group which may be substituted with a halogen; and $R^2$ represents hydrogen or an alkyl group having 1 to 2 carbon atoms which may be substituted with a halogen) from an ether compound represented by the formula (3): $R^1CH_2OCXYR^2$ (wherein $R^1$ and $R^2$ have the same meanings as described above; X represents fluorine or chlorine; and Y represents fluorine or chlorine).

Examples of the compound represented by the above formula (3) include 1,1-difluoro-1-methoxyethane, 1,1-difluoro-1-ethoxyethane, 1,1,2-trifluoro-1-methoxyethane, 1,1,2-trifluoro-1-ethoxyethane, 1,1,2,2-tetrafluoro-1-methoxyethane, 1,1,2,2-tetrafluoro-1-ethoxyethane, 1-chloro-1,1,2,2-tetrafluoro-2-methoxyethane, 1-chloro-1,1,2,2-tetrafluoro-2-ethoxyethane, and the like.

The antimony fluoride-supported aluminum fluoride as the dehalogenating agent may be suitably used in an excess amount relative to the compound represented by the above formula (3). Although the amount also depends on the ratio of the antimony fluoride to be supported, the fluoride may be, for example, used so that the antimony fluoride-supported aluminum fluoride becomes 0.1 g or more, and preferably from 1 g to 10 g, based on 1 mmol of the compound represented by the formula (5).

The mode of the reaction is not particularly limited as far as the compound represented by the above formula (3) comes into contact with the antimony fluoride-supported aluminum fluoride, In the batch-type, the reaction can be carried out by mixing both substances at a predetermined temperature. Moreover, an aliphatic hydrocarbon, an aromatic hydrocarbon, or the like can be used as a solvent. In the flow-type, the compound represented by the formula (3) may be passed through the antimony fluoride-supported aluminum fluoride at a predetermined temperature. Moreover, in this case, the compound represented by the formula (3) can be used after diluted with a diluting gas such as nitrogen gas or argon gas. The temperature of the reaction is from 100° C. to 300° C., and preferably from 150° C. to 250° C.

EXAMPLES

The present invention is described below in further detail with reference to Examples but the present invention is not limited by the following examples.

Example 1

Preparation of Antimony Fluoride-Supported Aluminum Fluoride:

A porous aluminum fluoride (hereinafter referred to as PAF) was prepared according to the method described in a literature (*Tetrahedron*, 57, 4111 (2002)). The resulting porous aluminum fluoride (surface area of 92 m$^2$/g, pore volume of 0.35 m$^3$/g) was dried by heating at 300° C. for at least 10 hors. Antimony pentachloride was gradually added dropwise to the dried porous aluminum fluoride under a nitrogen atmosphere to support antimony pentachloride thereon. By changing the amount for the dropwise addition, the supported amount of antimony pentachloride can be varied.

The porous aluminum fluoride on which antimony pentachloride had been supported was placed in a reaction tube (inner diameter of 12 mm, length of 300 mm) made of Inconel and was dried at 100° C. for 10 hours in a nitrogen stream (200 ml/min). Subsequently, anhydrous hydrofluoric acid (HF) diluted with nitrogen ($N_2$) was passed through at $N_2$/HF=100/100 (ml/min) at 100° C. for 2 hours and then at $N_2$/HF=100/200 (ml/min) at 200° C. for 2 hours. Thereafter, H alone was passed through at 200 ml/min at 200° C. for 3 hours and finally $N_2$ alone was passed through at 200 ml/min at 200° C. for 10 hours to remove remaining HF, whereby an antimony fluoride-supported aluminum fluoride (hereinafter referred to as Sb—F/PAF) was obtained. The resulting Sb—F/PAF can be stored not only in a plastic vessel but also in a glass vessel.

By this method, two kinds of Sb—F/PAF containing different supported amounts of antimony were prepared using 14 g and 55 g of antimony pentachloride relative to 40 g of porous aluminum fluoride. Hereinafter, they are referred to as Sb—F/PAF(A) and Sb—F/PAF(B), respectively. When the surface area and pore volume were measured on the resulting Sb—F/PAF(A) and Sb—F/PAF(B), Sb—F/PAF(A) had a surface area of 72 m$^2$/g and a pore volume of 0.31 m$^3$/g and Sb—F/PAF(B) had a surface area of 53 m$^2$/g and a pore volume of 0.20 m$^3$/g. Thus, it was confirmed that both of them maintained porosity. Moreover, the surface area and pore volume decrease as the supported amount of antimony pentachloride increases and this fact indicates that the antimony salt is present in the pores to fill the pores.

Moreover, XPS analysis (using C1s as a standard) was conducted on Sb—F/PAF(A) to obtain an element-existing ratio of C1s:13.3, F1s:66.4, A12p:15.7, C12p:0.1, and Sb3d5/2:4.5. Thereby, it was confirmed that the antimony salt was supported.

Furthermore, X-ray diffraction was measured on PAF, Sb—F/PAF(A), and Sb—F/PAF(B). The results are shown in (a), (b), and (c) of FIG. 1. From the results, it was confirmed that both of them maintained the porous structure of PAF since the same diffraction lines appeared in both of Sb—F/PAF(A) and Sb—F/PAF(B) as in PAF although partly different crystalline phase appeared in Sb—F/PAF(B).

Example 2

Figure 2:
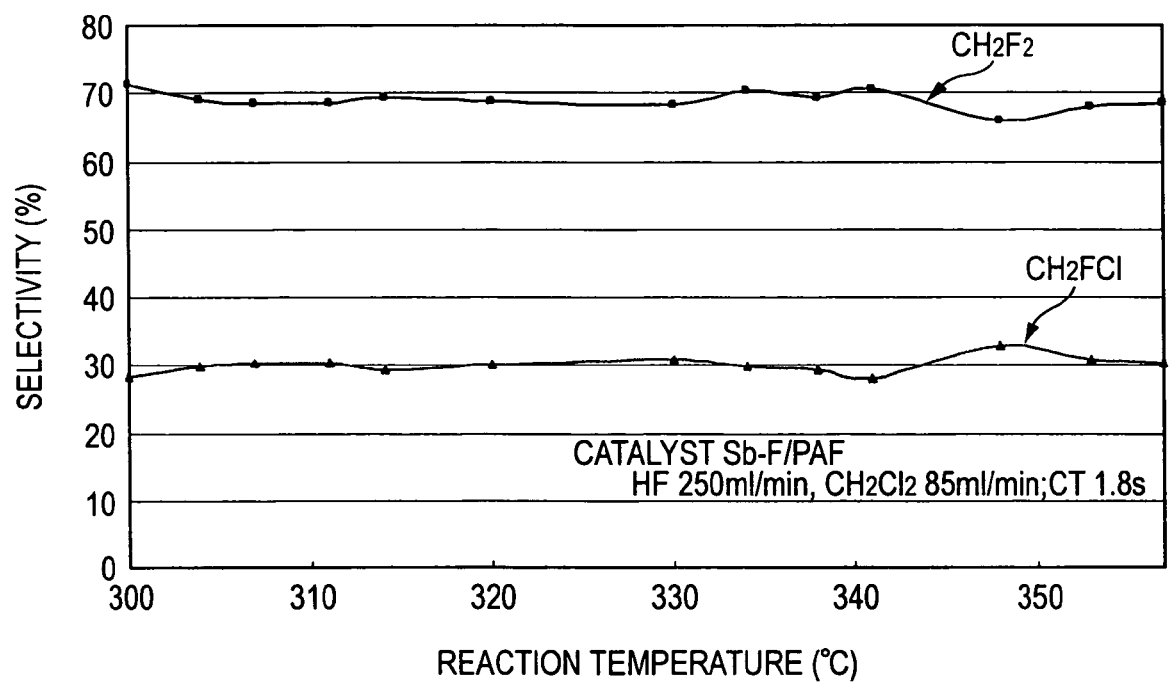
FIG. 2 is an analysis diagram of the fluoro compound obtained in Example 2 observed on a gas chromatography.

Synthesis of HFC-32 ($CH_2F_2$) from dichloromethane ($CH_2Cl_2$):

In a reaction tube (inner diameter of 12 mm, length of 300 mm) made of Inconel, 10 ml (8 g) of Sb—F/PAF(M) prepared in Example 1 was placed, and anhydrous hydrofluoric acid (HF) diluted with nitrogen ($N_2$) was passed through at $N_2$/HF=100/100 (ml/min) at 200° C. for 2 hours, then HF alone was passed through at 200 ml/min at 200° C. for 2 hours and further at 300° C. for 2 hours to activate Sb—F/PAF. Subsequently, $CH_2Cl_2$ was passed through at 85 ml/min and HF was passed through at 250 ml/min from one inlet to react them. The reaction temperature was raised from 300° C. to 350° C. gradually (10° C./h) and a mixed gas of product flowing out from another outlet was washed with an aqueous sodium hydroxide solution, dried over molecular sieve 4A, and then analyzed on a gas chromatography. The results of the analysis are shown in FIG. 2.

Example 3

Synthesis of HFC-143a ($CH_3CF_3$) from 1-chloro-1,1-difluoroethane ($CH_3CF_2Cl$):

In a reaction vessel made of stainless steel, 1 g of Sb—F/PAF(B) prepared in Example 1 was placed, and 2 mmol of $CH_3CF_2Cl$ was introduced under cooling at −196° C. The whole was heated to 200° C. and the temperature was maintained for 2 hours. The product was distilled by a trap-to-trap method to obtain 2 mmol (100%) of $CH_3CF_3$.

Example 4

Synthesis of HFC-143a ($CH_3CF_3$) from 1,1-dichloro-1-fluoroethane ($CH_3CFCl_2$):

The reaction was carried out in the same manner as in Example 3, except that $CH_3CFCl_2$ was used as a starting material, to obtain 1.6 mmol (82%) of $CH_3CF_3$.

Example 5

Synthesis of methyl chlorodifluoroacetate ($CH_3O(CO)CF_2Cl$) from 1-chloro-1,1,2,2-tetrafluoro-2-methoxyethane ($CH_3OCF_2CF_2Cl$):

The reaction was carried out in the same manner as in Example 3, except that $CH_3OCF_2CF_2Cl$ was used as a starting material, to obtain 1.34 mmol (67%) of $CH_3O(CO)CF_2Cl$.

INDUSTRIAL APPLICABILITY

The antimony fluoride-supported aluminum fluoride of the present invention is easy to handle, can be used for a flow-type reaction, and also can be used even at a high temperature and it can produce fluoro compounds such as hydrofluorocarbons and esters in high yields.

Therefore, the antimony fluoride-supported aluminum fluoride of the present invention is extremely useful as a fluorination catalyst, a fluorinating agent, a dehalogenating agent, and the like.

The invention claimed is:

1. A porous aluminum fluoride on which $SbCl_xF_{5-x}$ is supported, wherein x represents a numeral of 0 to 5, and wherein the porous aluminum fluoride on which the $SbCl_xF_{5-x}$ is supported does not contain hydrogen fluoride.

2. A process for producing the porous aluminum fluoride according to claim 1, comprising
    supporting $SbCl_yF_{5-y}$ on a porous aluminum fluoride, wherein y represents a numeral of 0 to 5;
    treating the supported $SbCl_yF_{5-y}$ with hydrogen floride; and
    removing remaining hydrogen fluoride from the treated supported $SbCl_yF_{5-y}$.

3. A fluorination catalyst comprising the porous aluminum fluoride according to claim 1.

4. A fluorinating agent comprising the porous aluminum fluoride according to claim 1.

5. A dehalogenating agent comprising the porous aluminum fluoride according to claim 1.

6. A process for producing a fluoro compound represented by the formula (2):

$$R^1R^2R^3CF$$

comprising reacting a compound represented by the formula (1):

$$R^1R^2R^3CX$$

with hydrogen fluoride in the presence of the catalyst according to claim 3, wherein
    $R^1$, $R^2$ and $R^3$ each represents hydrogen, a halogen, an alkyl group which may be substituted with a halogen or an ether group, or an alkoxy group: or $R^1$, $R^2$ and $R^3$ may be combined with each other to form a ring, and
    X represents chlorine, bromine or iodine.

7. A process for producing a fluoro compound represented by the formula (2):

$$R^1R^2R^3CF$$

comprising reacting a compound represented by the formula (1):

$$R^1R^2R^3CX$$

with the fluorinating agent according to claim 4, wherein
    $R^1$, $R^2$ and $R^3$ each represents hydrogen, a halogen, an alkyl group which may be substituted with a halogen or an ether group, or an alkoxy group: or $R^1$, $R^2$, and $R^3$ may be combined with each other to form a ring, and
    X represents chlorine, bromine or iodine.

8. A process for producing an ester represented by the formula (4):

$$R^1CH_2O(CO)R^2$$

comprising reacting an ether compound represented by the formula (3):

$$R^1CH_2OCXYR^2$$

with the dehalogenating agent according to claim 5, wherein
    $R^1$ represents hydrogen or an alkyl group which may be substituted with a halogen;
    $R^2$ represents hydrogen or an alkyl group which may be substituted with a halogen;
    X represents fluorine or chlorine; and
    Y represents fluorine or chlorine.

* * * * *